(12) United States Patent
Burkholz et al.

(10) Patent No.: US 9,579,486 B2
(45) Date of Patent: Feb. 28, 2017

(54) BLOOD CONTROL IV CATHETER WITH ANTIMICROBIAL PROPERTIES

(75) Inventors: Jonathan Karl Burkholz, Salt Lake City, UT (US); S. Ray Isaacson, Roy, UT (US); Marty L. Stout, South Jordan, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 13/591,897

(22) Filed: Aug. 22, 2012

(65) Prior Publication Data
US 2014/0058336 A1 Feb. 27, 2014

(51) Int. Cl.
| | |
|---|---|
| *A61M 5/14* | (2006.01) |
| *A61M 25/00* | (2006.01) |
| *A61M 39/10* | (2006.01) |
| *A61M 39/26* | (2006.01) |
| *A61M 39/16* | (2006.01) |

(52) U.S. Cl.
CPC ........ *A61M 25/0097* (2013.01); *A61M 39/10* (2013.01); *A61M 39/26* (2013.01); *A61M 39/162* (2013.01); *A61M 2025/0056* (2013.01); *A61M 2039/1072* (2013.01); *A61M 2039/267* (2013.01); *A61M 2205/0205* (2013.01)

(58) Field of Classification Search
CPC .......... A61M 2039/0036; A61M 39/62; A61M 39/26; A61M 202/0056; A61M 39/16; A61M 39/162; A61M 39/165
USPC ................................ 604/905, 240, 256, 533
See application file for complete search history.

(56) References Cited

U.S. PATENT DOCUMENTS

| | | | |
|---|---|---|---|
| 3,223,629 A | | 12/1965 | Loeffler |
| 3,986,508 A | * | 10/1976 | Barrington .................... 604/411 |
| 4,339,336 A | | 7/1982 | Hammond et al. |
| 4,387,879 A | | 6/1983 | Tauschinski |
| 4,449,693 A | | 5/1984 | Gereg |
| 4,512,766 A | | 4/1985 | Vailancourt |
| 4,584,192 A | | 4/1986 | Dell et al. |
| 4,592,920 A | * | 6/1986 | Murtfeldt ....................... 427/2.3 |
| 4,629,743 A | | 12/1986 | Hong |
| 4,629,746 A | | 12/1986 | Michl et al. |

(Continued)

FOREIGN PATENT DOCUMENTS

| | | |
|---|---|---|
| CA | 13313333 | 8/1994 |
| CA | 2133053 A1 | 3/1995 |

(Continued)

OTHER PUBLICATIONS

"ComfortCoat Hydrophilic Coating," DSM in Medical, http://www.dsm.com/en_US/medical/public/home/pages/product-coating-comfortcoat.jsp, Updated Jan. 11, 2013, Printed Apr. 22, 2013.

(Continued)

*Primary Examiner* — Edelmira Bosques
(74) *Attorney, Agent, or Firm* — Jeanne Lukasavage; Craig Metcalf; Kirton McConkie

(57) ABSTRACT

A medical device is presented, which includes a fluid pathway and a septum slidably housed within the fluid pathway. The septum can be opened by a septum actuator disposed in a fixed position within the fluid pathway. In some examples, both the septum actuator and the septum have at least one surface exposed to the fluid pathway. An anti-pathogenic material can be applied to these surfaces.

19 Claims, 7 Drawing Sheets

(56) References Cited

U.S. PATENT DOCUMENTS

| | | |
|---|---|---|
| 4,642,126 A | 2/1987 | Zador et al. |
| 4,677,143 A | 6/1987 | Laurin et al. |
| 4,716,032 A | 12/1987 | Westfall et al. |
| 4,758,225 A | 7/1988 | Cox et al. |
| 4,842,591 A | 6/1989 | Luther |
| 4,874,377 A | 10/1989 | Newgard et al. |
| 4,897,427 A | 1/1990 | Barnavon et al. |
| 4,915,934 A | 4/1990 | Tomlinson |
| 4,917,668 A | 4/1990 | Haindl |
| 4,925,668 A | 5/1990 | Khan et al. |
| 4,933,178 A | 6/1990 | Capelli |
| 4,935,010 A | 6/1990 | Cox et al. |
| 4,950,257 A | 8/1990 | Hibbs et al. |
| 5,023,082 A | 6/1991 | Friedman et al. |
| 5,041,097 A | 8/1991 | Johnson |
| 5,053,014 A | 10/1991 | Van Heugten |
| 5,062,836 A | 11/1991 | Wendell |
| 5,064,416 A | 11/1991 | Newgard et al. |
| 5,077,352 A | 12/1991 | Elton |
| 5,084,023 A | 1/1992 | Lemieux |
| 5,085,645 A | 2/1992 | Purdy et al. |
| 5,108,374 A | 4/1992 | Lemieux |
| 5,127,905 A | 7/1992 | Lemieux |
| 5,154,703 A | 10/1992 | Bonaldo |
| 5,156,596 A | 10/1992 | Balbierz et al. |
| 5,234,410 A | 8/1993 | Graham et al. |
| 5,290,246 A | 3/1994 | Yamamoto et al. |
| 5,295,969 A | 3/1994 | Fischell et al. |
| 5,330,435 A | 7/1994 | Vaillancourt |
| 5,350,363 A | 9/1994 | Goode et al. |
| 5,352,205 A | 10/1994 | Dales et al. |
| 5,405,323 A | 4/1995 | Rogers et al. |
| 5,456,675 A | 10/1995 | Wolbring et al. |
| 5,487,728 A | 1/1996 | Vaillancourt |
| 5,512,199 A | 4/1996 | Khan et al. |
| 5,520,666 A | 5/1996 | Choudhury et al. |
| 5,547,662 A | 8/1996 | Khan et al. |
| 5,549,566 A | 8/1996 | Elias et al. |
| 5,549,577 A | 8/1996 | Siegel et al. |
| 5,575,769 A | 11/1996 | Vaillancourt |
| 5,613,663 A | 3/1997 | Schmidt et al. |
| 5,616,338 A | 4/1997 | Fox, Jr. et al. |
| 5,629,006 A | 5/1997 | Hoang et al. |
| 5,651,772 A | 7/1997 | Arnett |
| 5,657,963 A | 8/1997 | Hinchliffe et al. |
| 5,697,915 A | 12/1997 | Lynn |
| 5,698,229 A | 12/1997 | Ohsumi et al. |
| 5,738,144 A | 4/1998 | Rogers |
| 5,749,861 A | 5/1998 | Guala et al. |
| 5,773,487 A | 6/1998 | Sokol |
| 5,806,831 A | 9/1998 | Paradis |
| 5,817,069 A | 10/1998 | Arnett |
| 5,861,440 A | 1/1999 | Gohla et al. |
| 5,911,710 A | 6/1999 | Barry et al. |
| 5,954,698 A | 9/1999 | Pike |
| 5,967,490 A | 10/1999 | Pike |
| 6,039,302 A | 3/2000 | Cote, Sr. et al. |
| 6,051,609 A | 4/2000 | Yu et al. |
| 6,077,244 A | 6/2000 | Botich et al. |
| 6,117,108 A | 9/2000 | Woehr et al. |
| 6,127,320 A | 10/2000 | van Ooij et al. |
| 6,171,287 B1 | 1/2001 | Lynn et al. |
| 6,242,526 B1 | 6/2001 | Siddiqui et al. |
| 6,248,811 B1 | 6/2001 | Ottersbach et al. |
| 6,273,869 B1 | 8/2001 | Vaillancourt |
| 6,326,417 B1 | 12/2001 | Jia |
| 6,337,357 B1 | 1/2002 | Fukunishi et al. |
| 6,353,041 B1 | 3/2002 | Qian |
| 6,413,539 B1 | 7/2002 | Shalaby |
| 6,485,473 B1 | 11/2002 | Lynn |
| 6,488,942 B1 | 12/2002 | Ingemann |
| 6,492,445 B2 | 12/2002 | Siddiqui et al. |
| 6,544,214 B1 * | 4/2003 | Utterberg .............. 604/93.01 |
| 6,575,960 B2 | 6/2003 | Becker et al. |
| 6,576,633 B1 | 6/2003 | Young et al. |
| 6,595,981 B2 | 7/2003 | Huet |
| 6,699,221 B2 | 3/2004 | Vaillancourt |
| 6,719,726 B2 | 4/2004 | Meng et al. |
| 6,740,063 B2 | 5/2004 | Lynn |
| 6,861,060 B1 | 3/2005 | Luriya et al. |
| 6,883,778 B1 | 4/2005 | Newton et al. |
| 6,896,889 B2 | 5/2005 | Chevalier et al. |
| 7,008,404 B2 | 3/2006 | Nakajima |
| 7,074,839 B2 | 7/2006 | Fansler et al. |
| 7,098,256 B2 | 8/2006 | Ong et al. |
| 7,179,849 B2 | 2/2007 | Terry |
| 7,198,800 B1 | 4/2007 | Ko |
| 7,232,540 B2 | 6/2007 | Gould et al. |
| 7,261,925 B2 | 8/2007 | Nesbitt |
| 7,347,839 B2 | 3/2008 | Hiejima |
| 7,396,346 B2 | 7/2008 | Nakajima |
| 7,407,707 B2 | 8/2008 | Gould et al. |
| 7,462,401 B2 | 12/2008 | Halfyard et al. |
| 7,470,254 B2 | 12/2008 | Basta et al. |
| 7,494,339 B2 | 2/2009 | Dias et al. |
| 7,498,367 B2 | 3/2009 | Qian |
| 7,514,477 B2 | 4/2009 | Klare et al. |
| 7,736,339 B2 | 6/2010 | Woehr et al. |
| 7,816,434 B2 | 10/2010 | Hackbarth et al. |
| 7,914,494 B2 | 3/2011 | Hiejima |
| 8,034,455 B2 | 10/2011 | Wang et al. |
| 8,227,050 B1 | 7/2012 | O'Neil |
| 8,263,102 B2 | 9/2012 | Labrecque et al. |
| 8,388,583 B2 | 3/2013 | Stout et al. |
| 8,512,294 B2 * | 8/2013 | Ou-Yang et al. ........ 604/167.04 |
| 8,840,927 B2 | 9/2014 | DiTizio et al. |
| 2001/0016589 A1 | 8/2001 | Modak et al. |
| 2001/0018095 A1 * | 8/2001 | Shlenker et al. ............. 427/337 |
| 2001/0053895 A1 | 12/2001 | Vaillancourt |
| 2001/0056133 A1 | 12/2001 | Montgomery et al. |
| 2002/0022660 A1 | 2/2002 | Jampani et al. |
| 2002/0028751 A1 | 3/2002 | Lokkesmoe et al. |
| 2002/0040092 A1 | 4/2002 | Siddiqui et al. |
| 2002/0119111 A1 | 8/2002 | Kilgour et al. |
| 2002/0144705 A1 | 10/2002 | Brattesani et al. |
| 2003/0072781 A1 | 4/2003 | Pelerin |
| 2003/0119932 A1 | 6/2003 | Al-Akhdar et al. |
| 2003/0147932 A1 | 8/2003 | Nun et al. |
| 2003/0162839 A1 | 8/2003 | Symington et al. |
| 2003/0170308 A1 | 9/2003 | Cleary et al. |
| 2004/0014864 A1 | 1/2004 | Milic et al. |
| 2004/0039349 A1 | 2/2004 | Modak et al. |
| 2004/0058829 A1 | 3/2004 | Hei et al. |
| 2004/0115477 A1 | 6/2004 | Nesbitt |
| 2004/0185296 A1 | 9/2004 | Mazzanti |
| 2004/0234475 A1 | 11/2004 | Lannibois-Drean et al. |
| 2005/0048005 A1 | 3/2005 | Stockel |
| 2005/0080158 A1 | 4/2005 | Ong et al. |
| 2005/0100580 A1 | 5/2005 | Osborne et al. |
| 2005/0265931 A1 | 12/2005 | Qian |
| 2006/0051385 A1 | 3/2006 | Scholz |
| 2006/0163515 A1 | 7/2006 | Ruschke |
| 2006/0165751 A1 | 7/2006 | Chudzik et al. |
| 2006/0165903 A1 | 7/2006 | Mazzanti |
| 2006/0239954 A1 | 10/2006 | Sancho |
| 2006/0258780 A1 | 11/2006 | Chaussade et al. |
| 2006/0281663 A1 | 12/2006 | Asmus |
| 2007/0000407 A1 | 1/2007 | Leong |
| 2007/0083157 A1 | 4/2007 | Belley et al. |
| 2007/0083162 A1 | 4/2007 | O'Reagan et al. |
| 2007/0112112 A1 | 5/2007 | Kerschner et al. |
| 2007/0112146 A1 | 5/2007 | Falk et al. |
| 2007/0141524 A1 | 6/2007 | Brennan et al. |
| 2007/0160547 A1 | 7/2007 | Duffy et al. |
| 2007/0166344 A1 | 7/2007 | Qu et al. |
| 2007/0202177 A1 | 8/2007 | Hoang |
| 2007/0203574 A1 | 8/2007 | McGrath et al. |
| 2007/0225179 A1 | 9/2007 | Schutz et al. |
| 2007/0233007 A1 | 10/2007 | Adams |
| 2007/0275101 A1 | 11/2007 | Lu et al. |
| 2008/0026026 A1 | 1/2008 | Lu et al. |
| 2008/0039796 A1 | 2/2008 | Nakajima |
| 2008/0075761 A1 | 3/2008 | Modak et al. |
| 2008/0108944 A1 | 5/2008 | Woehr et al. |

(56) References Cited

U.S. PATENT DOCUMENTS

| | | | |
|---|---|---|---|
| 2008/0161763 A1 | 7/2008 | Harding et al. | |
| 2008/0182921 A1 | 7/2008 | Suh et al. | |
| 2009/0110844 A1 | 4/2009 | Platzer et al. | |
| 2009/0114327 A1 | 5/2009 | Breunig | |
| 2009/0117164 A1 | 5/2009 | Toreki et al. | |
| 2009/0162530 A1 | 6/2009 | Nesbitt | |
| 2009/0176907 A1 | 7/2009 | Subramanian et al. | |
| 2009/0188559 A1 | 7/2009 | Nesbitt | |
| 2009/0220739 A1 | 9/2009 | Chougule | |
| 2009/0226541 A1 | 9/2009 | Scholz et al. | |
| 2009/0317435 A1 | 12/2009 | Vandesteeg et al. | |
| 2009/0324666 A1 | 12/2009 | Krongauz et al. | |
| 2010/0135949 A1 | 6/2010 | Ou-Yang | |
| 2010/0136209 A1 | 6/2010 | Ou-Yang et al. | |
| 2010/0137379 A1 | 6/2010 | Ou-Yang | |
| 2010/0137472 A1 | 6/2010 | Ou-Yang | |
| 2010/0204648 A1* | 8/2010 | Stout et al. | 604/122 |
| 2010/0204675 A1 | 8/2010 | Woehr et al. | |
| 2010/0222746 A1 | 9/2010 | Burkholz | |
| 2011/0009831 A1 | 1/2011 | Burkholz et al. | |
| 2011/0065798 A1 | 3/2011 | Hoang et al. | |
| 2011/0160663 A1 | 6/2011 | Stout et al. | |
| 2011/0218529 A1* | 9/2011 | Garcia et al. | 606/41 |
| 2011/0319825 A1* | 12/2011 | Goral et al. | 604/164.01 |

FOREIGN PATENT DOCUMENTS

| | | |
|---|---|---|
| CN | 1526771 A | 9/2004 |
| CN | 101353545 A | 1/2009 |
| CN | 102070983 A | 5/2011 |
| DE | 40 11 867 A1 | 10/1991 |
| DE | 20 2009 009 602 U1 | 12/2009 |
| EP | 0 338 418 A1 | 10/1989 |
| EP | 0 379 271 A2 | 7/1990 |
| EP | 0 414 997 A1 | 3/1991 |
| EP | 1 679 043 A1 | 7/2006 |
| JP | 07-051651 | 2/1995 |
| JP | 08-209064 | 8/1996 |
| JP | 8-311373 A | 11/1996 |
| JP | 09-157548 | 6/1997 |
| JP | 2000-178475 A | 6/2000 |
| JP | 2000-264803 A | 9/2000 |
| JP | 2001-072438 A | 3/2001 |
| JP | 2004-043669 A | 2/2004 |
| JP | 2005-028209 A | 2/2005 |
| JP | 2005-520912 A | 7/2005 |
| JP | 2007-016096 A | 1/2007 |
| KR | 2002-0066429 A | 8/2002 |
| WO | 98/58690 | 12/1998 |
| WO | 98/58989 | 12/1998 |
| WO | 99/32168 | 7/1999 |
| WO | 99/34849 | 7/1999 |
| WO | 00/66189 | 11/2000 |
| WO | 2006/056482 A1 | 6/2006 |
| WO | 2006/074666 A2 | 7/2006 |
| WO | WO 2006088288 A1 * | 8/2006 |
| WO | 2006/099358 A2 | 9/2006 |
| WO | 2007/095576 A2 | 8/2007 |
| WO | 2007/100653 A2 | 9/2007 |
| WO | 2007/100776 A2 | 9/2007 |
| WO | 2008/014438 A2 | 1/2008 |
| WO | 2008/014447 A2 | 1/2008 |
| WO | 2008/045761 A2 | 4/2008 |
| WO | 2008/052790 A2 | 5/2008 |
| WO | 2008/128896 A2 | 10/2008 |
| WO | 2008/132045 A2 | 11/2008 |
| WO | 2009/070227 A1 | 6/2009 |
| WO | 2009/114833 A1 | 9/2009 |
| WO | 2010/093791 A1 | 8/2010 |

OTHER PUBLICATIONS

"Lubricent—Lubricious Hydrophillic Coatings for Medical Devices," Harland Medical Systems, http://www.harlandmedical.com/index.php/materials/lubricent.html, pp. 1-2, Printed Apr. 22, 2013.

"UV & EB Cure," Xiper Innovations, Inc., http://xiperinnovations.com/uv_eb_cure, Printed Apr. 22, 2013.

Cabot Corporation, "Using Silicas and Aluminas in Coatings,", www.cabot-corp.com/Silicas-And-Aluminas/Coatings, downloaded from the internet on Apr. 26, 2011.

Elson Silva, PhD, "Respecting Hydrology Science in the Patenting System," pp. 1-7, Jan. 13, 2011.

McDonnell, G., Russell, A.D. Antiseptics and Disinfectants: Activity, Action, and Resistance. Clinical Microbiology Reviews, (1999) 12(1), pp. 149-179.

* cited by examiner ent invention relates to systems and methods for selec-

BLOOD CONTROL IV CATHETER WITH ANTIMICROBIAL PROPERTIES

BACKGROUND OF THE INVENTION

The current invention relates to systems and methods for coating various surfaces of medical devices with an antipathogenic material. In particular, the present invention relates to systems and methods for applying anti-pathogenic material to select interior surfaces to reduce or eliminate pathogenic colonization and growth within the medical device.

A formidable challenge of modern medical treatment is control of infection in the spread of pathogenic organisms. One area where this challenge is constantly presented is in infusion therapy of various types. Infusion therapy is one of the most common healthcare procedures. Hospitalized, home care, and other patients receive fluids, pharmaceuticals, and blood products via a vascular access device inserted into the vascular system of the patient. Infusion therapy may be used to treat an infection, provide anesthesia or analgesia, provide nutritional support, treat cancerous growths, maintain blood pressure and heart rhythm, or many other clinically significant uses.

Infusion therapy is facilitated by a vascular access device. The vascular access device may access the patient's peripheral or central vasculature. The vascular access device may be indwelling for short-term (days), moderate term (weeks), or long-term (months to years). The vascular access device may be used for continuous infusion therapy or for intermittent therapy.

A common vascular access device comprises a plastic catheter inserted into a patient's vein. The catheter length may vary from a few centimeters for peripheral access, to many centimeters for central access and may include devices such as peripherally inserted central catheters (PICC). The catheter may be inserted transcutaneously or may be surgically implanted beneath the patient's skin. The catheter, or any other vascular access device attached thereto, may have a single lumen or multiple lumens for infusion of many fluids simultaneously.

A vascular access device may serve as a nidus, resulting in a disseminated BSI (blood stream infection). This may be caused by failure to regularly flush the device, a non-sterile insertion technique, or by pathogens that enter the fluid flow path through either end of the path subsequent to catheter insertion. When a vascular access device is contaminated, pathogens adhere to the vascular access device, colonize, and form a biofilm. The biofilm is resistant to most biocidal agents and provides a replenishing source of pathogens to enter a patient's bloodstream and cause a BSI.

One approach to preventing biofilm formation and patient infection is to provide an anti-pathogenic coating on various medical devices and components. However, some medical devices and components comprise materials or features which are incompatible with anti-pathogenic coatings. Thus, although methods exist for providing an anti-pathogenic coating on various medical devices and components, challenges still exist. Accordingly, it would be an improvement in the art to augment or even replace current techniques with other techniques. Such techniques are disclosed herein.

BRIEF SUMMARY OF THE INVENTION

In order to overcome the limitations discussed above, the present invention relates to systems and methods for selectively coating surfaces of medical devices that contact blood or other fluids as part of an infusion therapy.

Some implementations of the present invention include a medical device having a fluid pathway. A septum is slidably housed within the fluid pathway. A septum actuator is disposed in a fixed position within the fluid pathway. In operation, the septum can be advanced toward the septum actuator, which can pierce the septum, opening the septum and permitting fluid flow therethrough. In some examples, both the septum actuator and the septum have at least one surface exposed to the fluid pathway. An anti-pathogenic material can be applied to these surfaces.

In some instances, the septum has a tubular shape and has a barrier member. The septum can thus form a proximal cavity. The barrier member can have a slit extending between a distal and proximal side of the barrier member. The barrier member can divide the septum into the proximal cavity and a distal cavity, and a portion of the septum actuator can be disposed within the distal cavity.

In some implementations, an anti-pathogenic material including a lubricant agent is applied to the probe portion of the septum actuator to reduce friction between the septum actuator and the septum during activation of the device. In other implementations, a rigid or semirigid anti-pathogenic material is applied to various surfaces of a base portion of the septum actuator.

Certain aspects of the present invention further include a color code system, whereby the identity of the anti-pathogenic material is identified based upon the color of the medical device.

In other aspects of the present invention, a ventilation channel can be interposed between the septum and an inner surface of the infusion therapy device. The anti-pathogenic material can be applied to a surface of the ventilation channel. The anti-pathogenic material applied to the surface of the ventilation channel can have a thickness less than that which would occlude the ventilation channel to permit venting through the ventilation channel.

Some aspects of the present invention include a medical device having a compatible surface that includes at least one mechanical bond to facilitate binding between the surface and an anti-pathogenic material. Other aspects of the invention include providing a chemical bond between a compatible surface of a medical device and an anti-pathogenic material by surface cross-linking.

The present invention further includes various methods, techniques, and materials for identifying and coating surfaces of medical devices which include noncritical dimensions. Thus, an anti-pathogenic material may be applied to various surfaces within a medical device to reduce or eliminate pathogenic colonization and/or growth within the medical device thereby reducing the risk of pathogenic infection in patients.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

DETAILED DESCRIPTION OF THE INVENTION

Figure 1:
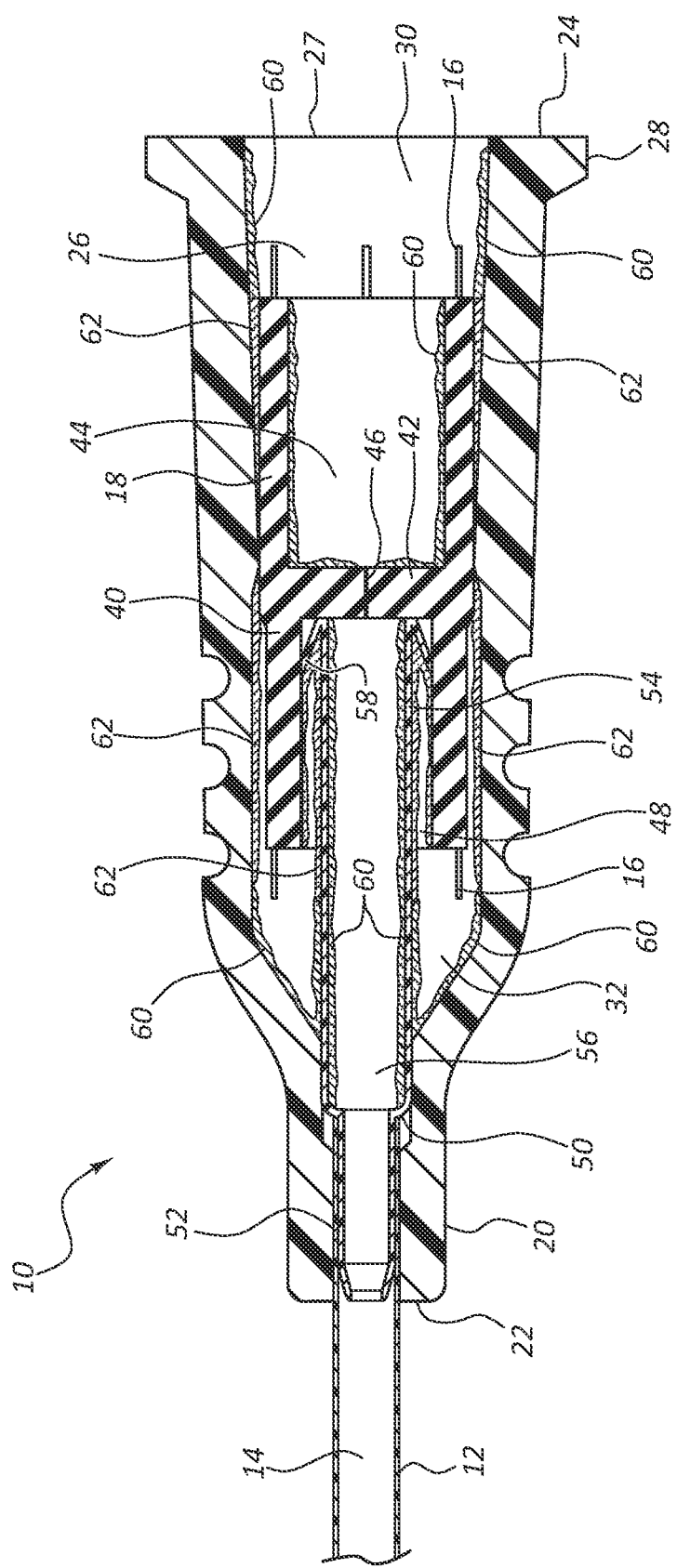
FIG. 1 is a cross-section view of a catheter assembly comprising a septum and septum actuator prior to activation, the catheter assembly, septum, and septum actuator having various surfaces with critical and noncritical dimensions in accordance with a representative embodiment of the present invention.

The presently preferred embodiment of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

The term "proximal" is used to denote a portion of a device which, during normal use, is nearest the user and furthest from the patient. The term "distal" is used to denote a portion of a device which, during normal use, is farthest away from the user wielding the device and closest to the patient. The term "activation" of valve mechanism or septum is used to denote the action of opening or closing of such valve. For example, in some embodiments a catheter assembly is provided having a septum and a septum actuator, wherein the catheter assembly undergoes activation when the septum actuator is advanced through the septum, thereby providing a fluid pathway through the septum.

The term "critical dimension" is used to denote at least one of a height, a length, a width, a depth, a diameter, a thickness, an angle, a texture, or other structural feature of a surface of a medical device which is critical to the operation of the device. For example, in some embodiments a medical device may include a surface that is configured to interface with another device or component. As such, the surface may include a critical dimension that is configured to accommodate optimal interaction between the surface of the medical device and the interfacing device or component. Thus, in some embodiments a surface having a critical dimension must remain unmodified to preserve the intended and/or desired interaction of the surface in operating or using the medical device. Conversely, the term "noncritical dimension" is used to denote at least one of a height, a length, a width, a depth, a diameter, a thickness, an angle, a texture, or other structural feature of a medical device with is not critical to the operation of the device.

The terms "chemical bond" or "chemical bonding" are used to denote an attraction between atoms that allows an anti-pathogenic material to be applied to a desired surface of a medical device. For example, in some instances an anti-pathogenic material of the present invention is applied to the surface of an infusion therapy medical device via chemical bonding, wherein atoms of the anti-pathogenic material and atoms of the medical device are chemically attracted to one another. Chemical bonding may include any type of atomic bond, such as a covalent bond, an ionic bond, dipole-dipole interactions, London dispersion force, Van der Waals force, and hydrogen bonding. A chemical bond may further be denoted by the terms "cross-linking" or "surface cross-linking" for some embodiments.

The terms "mechanical bond" or "mechanical bonding" are used to denote a physical, non-chemical interaction between two or more materials. For example, in some instances a surface of a medical device is altered to include a texture, a groove, and/or a ridge having a void which holds an anti-pathogenic material via capillary force. In other embodiments, a mechanical bond comprises a structural feature which provides increased surface area to a surface of a medical device. Further, in some embodiments, a mechanical bond comprises a hydrophilic or hydrophobic material or coating that is applied to a surface of a medical device to attract an anti-pathogenic material. A mechanical bond may further be denoted by the term "mechanical interlock" for some embodiments.

The term "compatible surface" is used to denote a surface of a medical device which includes a noncritical dimension, or a surface which includes a critical dimension that will not be adversely affected by the addition of an anti-pathogenic material or coating.

The terms "rigid" or "semirigid" are used to denote a physical property of an anti-pathogenic material, wherein the material is deficient in, or devoid, or mostly devoid of flexibility. Alternatively, these terms are used to denote an inflexible or mostly inflexible physical property of an anti-pathogenic material when applied or coated onto a surface of a device. In some instances, the term semirigid is understood to describe a physical property of an anti-pathogenic material that is rigid to some degree or in some parts.

The term "modified rheology" is used to denote a physical property of an anti-pathogenic material, wherein the viscosity of an anti-pathogenic material is modified to prevent excessive migration of the anti-pathogenic material once applied to a surface of a device. As such, the modified rheology of the anti-pathogenic material prevents or substantially prevents contact between the anti-pathogenic material and adjacent surfaces or components.

The term "anti-pathogenic" is used to denote a material, such as a coating material, that acts against pathogens. Pathogens may include any organism or substance capable of causing a disease, such as bacteria, viruses, protozoa and fungi. Accordingly, an "anti-pathogenic material" as contemplated herein includes any material having properties for acting against a pathogen.

The present invention relates generally to systems and methods for applying anti-pathogenic materials to various surfaces of medical devices. In particular, the present invention relates to systems and methods for applying antipathogenic materials to surfaces of medical devices for infusion therapies, wherein the surface comprises a portion of a fluid pathway of the medical device. In some instances, an anti-pathogenic material is applied to a surface comprising a noncritical dimension. In some embodiments, an anti-pathogenic material is applied to one or more surfaces of a medical device prior to assembling the medical device. In other embodiments, an anti-pathogenic material is applied to the first portion or component of a medical device and subsequently transferred to a second portion or component of the medical device through controlled migration of the anti-pathogenic material. In other instances, an anti-pathogenic material is intermixed with, or incorporated into the material of the medical device during a molding process of the device. Further, in some instances an anti-pathogenic material is applied to or incorporated into the material of a medical device such that the anti-pathogenic material elutes out from the material of the medical device into the immediate surroundings of the coated medical device.

In general, an anti-pathogenic material in accordance with the present invention may include any material having anti-pathogenic properties which may be applied to the surface of a medical device, such as an infusion therapy device. For example, in some embodiments an anti-pathogenic material may include an antimicrobial composition, as taught in U.S. patent application Ser. Nos. 12/397,760, 11/829,010, 12/476,997, 12/490,235, and 12/831,880, each of which is incorporated herein by reference, in its entirety. In some embodiments, an anti-pathogenic material may further include an anti-infective or antimicrobial lubricant, as taught in U.S. patent application Ser. Nos. 12/436,404 and 12/561,863, each of which is incorporated herein in its entirety. Further, in some embodiments an anti-pathogenic material is incorporated into the material of a medical device, or a component thereof, such as a septum actuator.

Some embodiments of the present invention comprise a medical device or component having at least one surface that defines a portion of a fluid pathway through the medical device, such as an infusion therapy device (e.g., a catheter assembly or Luer adapter). The surface of the medical device is coated with an anti-pathogenic material to prevent colonization of pathogens on the coated surface.

The application of an anti-pathogenic material to the surface of a medical device results in the addition of a layer or "coat" of anti-pathogenic material to the surface. This layer of anti-pathogenic material has a dimension (i.e. thickness) which may affect a relationship between the coated surface and an interfacing or adjacent component of the medical device. For example, in some embodiments a medical device may include an aperture having a diameter to compatibly receive a second medical device, such as by a friction, press, mechanical or interference fit. As such, the diameter of the aperture includes critical dimensions to ensure proper fitting between the aperture and the second medical device. In this example, the addition of an anti-pathogenic material to the surface of the aperture will adjust the diameter of the aperture thereby adversely affecting the ability of the aperture to receive the second medical device.

Accordingly, in some embodiments of the present invention it is undesirable to modify or coat a surface of a medical device or component wherein the surface includes a critical dimension that will be adversely affected by the addition of the anti-pathogenic material. Thus, some embodiments of the present invention comprise a method for coating a medical device with an anti-pathogenic material, wherein the method includes a first step of identifying surfaces of the medical device which include noncritical dimensions. The method may further include a step whereby the surfaces having noncritical dimensions are then coated with an anti-pathogenic material. Some methods of the present invention may further include steps for identify and isolating surfaces of the medical device having critical dimensions, prior to coating the remaining surfaces with an anti-pathogenic material.

Figure 2:
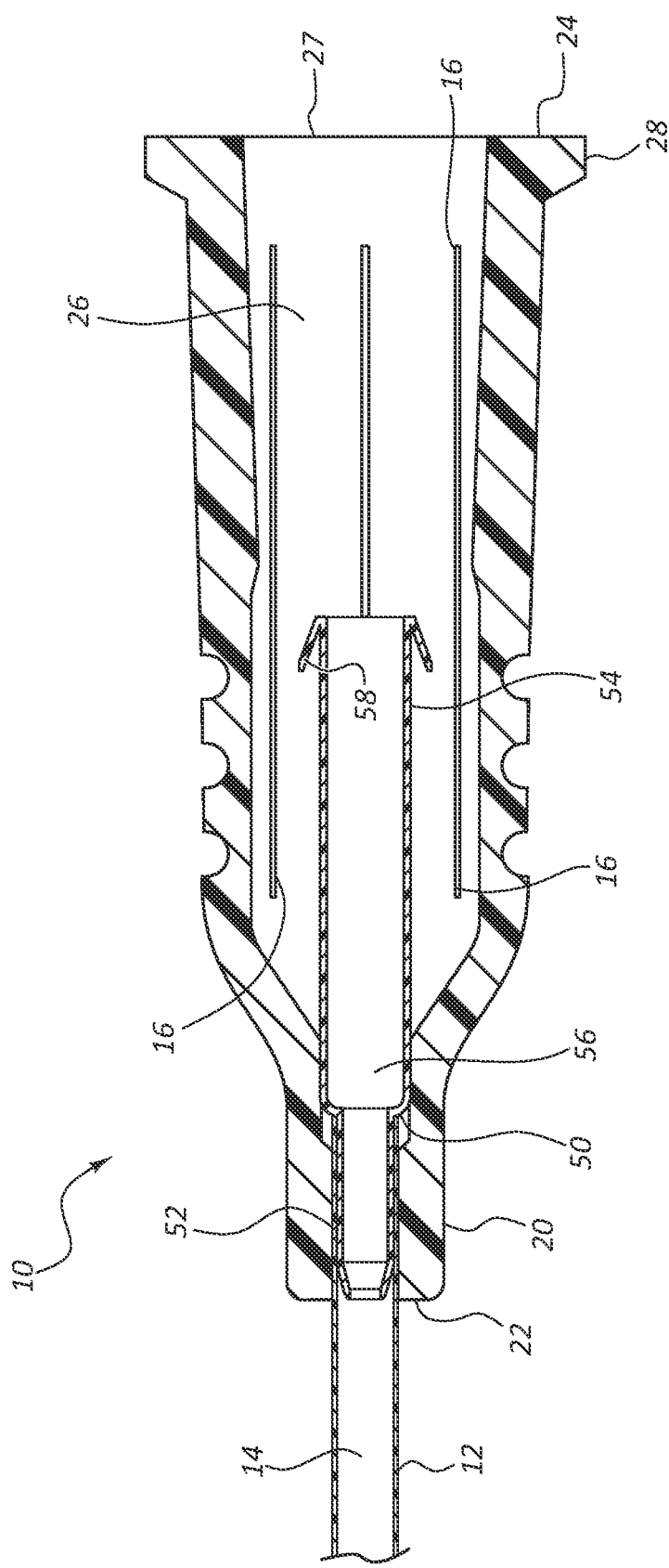
FIG. 2 is a cross-section view of the catheter assembly of FIG. 1, with the septum and anti-pathogenic material removed, showing internal ventilation channels in accordance with a representative embodiment of the present invention.
Figure 3:
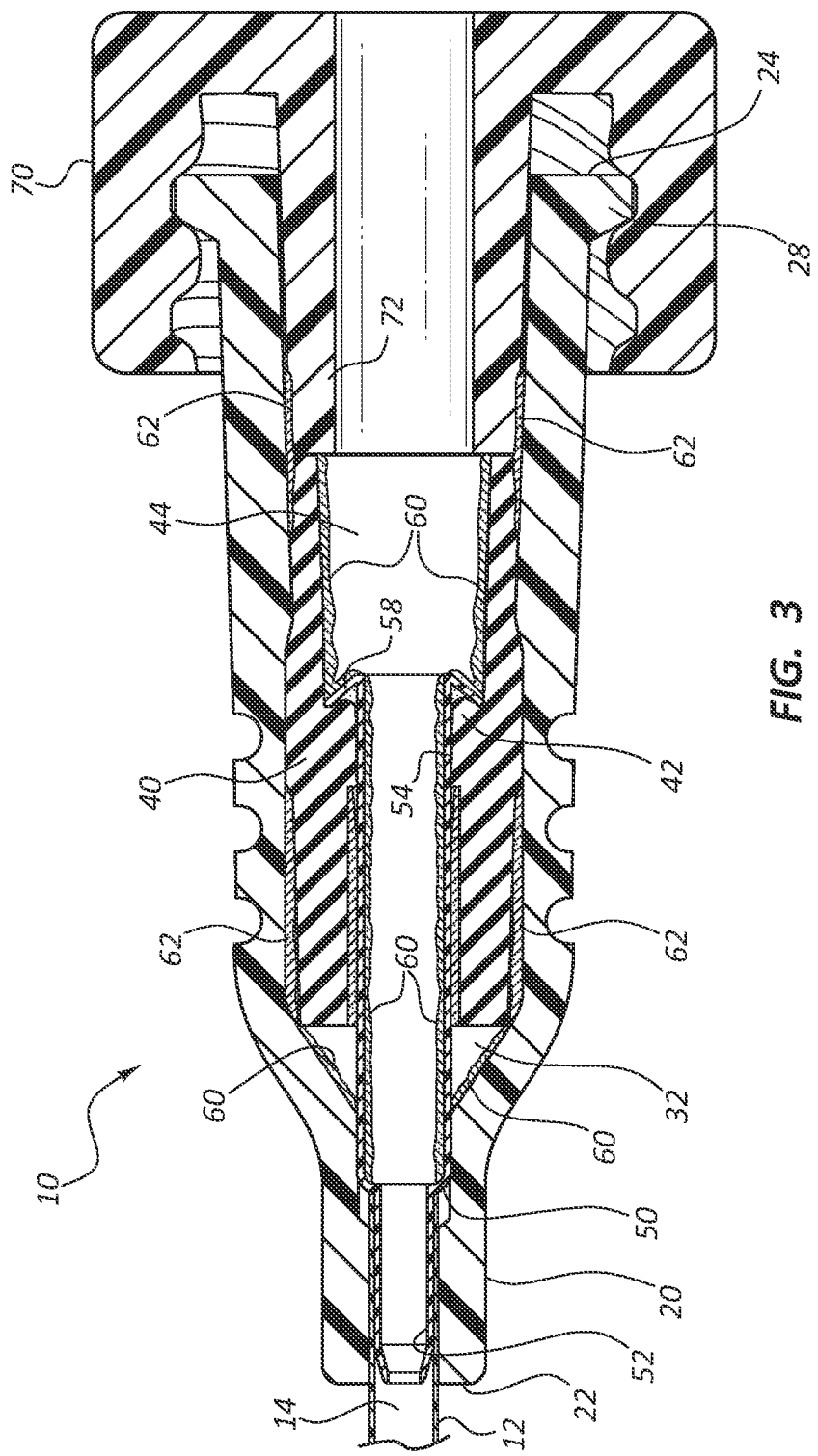
FIG. 3 is a cross-section view of the catheter assembly of FIG. 1 comprising a septum and septum actuator following activation in accordance with a representative embodiment of the present invention.

In further examples of the teachings of the present invention, a catheter assembly device 10 is shown in FIGS. 1-3. Catheter assembly device 10 provides a non-limiting example of a medical device having various surfaces which may be coated with an anti-pathogenic material. Accordingly, catheter assembly device 10 provides a representative embodiment on which to demonstrate and discuss the methodologies of the present invention relating to the selection and coating of surfaces with an anti-pathogenic material.

Referring now to FIG. 1, a cross-section view of a catheter assembly 10 is shown. Catheter assembly 10 generally includes a catheter 12 coupled to a distal end 22 of a catheter adapter 20. Catheter 12 and catheter adapter 20 are integrally coupled such that an internal lumen 26 of catheter adapter 20 is in fluid communication with a lumen 14 of catheter 12. Catheter 12 generally comprises a biocompatible material having sufficient rigidity twisting pressures associated with insertion of the catheter into a patient. In some embodiments, catheter 12 comprises a metallic material, such as titanium, stainless steel, nickel, molybdenum, surgical steel, and alloys thereof. In other embodiments, catheter 12 comprises a rigid, polymer material, such as vinyl or silicon.

Catheter assembly 10 may further include features for use with an over-the-needle catheter assembly. For example, a flexible or semi flexible polymer catheter may be used in combination with a rigid introducer needle to enable insertion of the catheter into the vasculature of a patient. Surgically implanted catheters may also be used.

Once inserted into a patient, catheter 12 and catheter adapter 20 provide a fluid conduit to facilitate delivery of a fluid to and/or retrieval of a fluid from a patient, as required by a desired infusion procedure. Thus, in some embodiments the material of the catheter 12 and the catheter adapter 20 are selected to be compatible with bio-fluids and medicaments commonly used in infusion procedures. Additionally, in some embodiments a portion of the catheter 12 and/or catheter adapter 20 is configured for use in conjunction with a section of intravenous tubing (not shown) to further facilitate delivery of a fluid to or removal of a fluid from a patient.

The various embodiments of the present invention may be adapted for use with any medical device or accessory having a lumen in which is placed a septum. For example, in some embodiments a female Luer adapter coupled to a section of intravenous tubing may comprise a septum and a septum actuator in accordance with the present teachings. In other embodiments, one or more ends of a y-port adapter may comprise a septum and a septum actuator in accordance with the teachings of the present invention.

In some embodiments, a proximal end 24 of the catheter adapter 20 includes a flange 28. Flange 28 provides a positive surface which may be configured to enable coupling of intravenous tubing or a Luer adapter to the catheter assembly 10. In some embodiments, flange 28 further includes a set of threads to accept a Luer adapter via a threaded connection.

In some embodiments, a septum 40 can be slidaby housed with internal lumen 26 of catheter adapter 20. Septum 40 generally comprises a flexible or semi-flexible polymer plug having an outer diameter that is configured to fit within internal lumen 26. In some embodiments, septum 40 is tube shaped having one or more internal cavities. In some embodiments, barrier surface 42 is disposed between a distal end and a proximal end of the septum 40 can divide the interior of septum 40 into a proximal cavity 44 and a distal cavity 48. In other embodiments, barrier surface 42 can be disposed at or near the distal or proximal end of septum 40. A slit 46 can be formed in barrier surface 42 for selectively opening fluid communication between proximal cavity 44 and distal cavity 48. As shown, some septum embodiments have a substantially H-shaped cross section. When positioned within catheter adapter 20, barrier surface 42 divides inner lumen 26 of catheter adapter 20 into a proximal fluid chamber 30 and a distal fluid chamber 32. Thus, the presence of septum 40 can control or limit passage of fluid between the proximal and distal fluid chambers 30 and 32. As shown, septum 40 can be held in place within internal lumen 26 via contact with one or more inner surfaces of the internal lumen, contact with anti-pathogenic material, and/or contact with probe 54 of septum actuator 50.

In some embodiments, catheter assembly 10 further comprises a septum actuator 50. Septum actuator 50 is generally fixedly positioned within distal fluid chamber 32 and has a portion that is positioned adjacent septum 40. In some instances, septum actuator 50 comprises a base 52 that is coupled to catheter adapter 20. For example, as shown, base 52 can be at least partially inserted into the proximal end of catheter 12. In that configuration, base 52 acts as a wedge forming a press fit between catheter 12 and catheter adapter 20 to, at least partially, retain catheter 12 and base 52 in place. In another example, base 52 can be coupled directly to catheter adapter 20 via a fastener, adhesive, bonding technique, or molding. As shown, septum actuator 50 can have a tubular configuration with a hollow interior that forms a lumen 56 in fluid communication with lumen 14 of catheter 12. As further shown, septum actuator 50 further comprises a probe 54 which is positioned adjacent barrier surface 42 of septum 40 prior to activation of catheter assembly 10. Probe 54 can include barbs or other features for preventing proximal movement of septum 40 after septum activation.

In some embodiments, septum actuator 50 may comprise various features to facilitate use of septum actuator 50 within catheter assembly 10. For example, septum actuator 50 may include various vents 16 and other structural features to control fluid flow through and around septum actuator 50, as taught in U.S. patent application Ser. Nos. 12/703,336 and 12/703,406, each of which is incorporated herein by reference, in its entirety.

In some embodiments, septum 40 is slidably housed within catheter adapter 20, such that septum 40 comprises an independent component of catheter assembly 10. As such, septum 40 is capable of being advanced in a distal direction, in which septum actuator 50 pierces through slit 46, opening a fluid path through septum 40. This process is illustrated in FIG. 3 and described in greater detail with reference to that figure.

In some embodiments, septum 40 and/or septum actuator 50 may be coated with an anti-pathogenic material prior to being inserted into catheter adapter 20. In some instances, septum 40 and/or septum actuator 50 is coated with a rigid or semirigid anti-pathogenic material such that fluid which bypasses these structures comes in contact with the anti-pathogenic material. In other instances, septum 40 and/or septum actuator 50 is coated with a viscous or fluid anti-pathogenic material such that the anti-pathogenic material is transferred to surfaces of catheter assembly 10 which come in contact with the anti-pathogenic material. Further still, in some instances the material of septum 40 and/or septum actuator 50 comprises an anti-pathogenic material or agent. For example, the material of septum actuator 50 may include an anti-pathogenic material which is incorporated into or and mixed with the material of septum actuator 50 during a manufacturing process. In some instances, the anti-pathogenic material is capable of eluding out of septum 40 or septum actuator 50 into the surrounding areas within the catheter adapter 20. For example, a fluid passing through catheter adapter 20 may be treated with the anti-pathogenic material of septum actuator 50 by either directly contacting the anti-pathogenic material or by contacting anti-pathogenic material which has eluded from the material of septum actuator 50.

In some embodiments, a septum 40 and septum actuator 50 are provided within a fluid pathway of catheter assembly 10, such that all fluid passing through catheter assembly 10 come in contact with septum 40 and septum actuator 50, or pass in proximity to these structures through their immediate surroundings. Thus, some embodiments of the present invention provide anti-pathogenic treatment of a fluid within catheter assembly 10 by providing a septum 40 and/or septum actuator 50 having an external or exposed surface which is coated with anti-pathogenic material. Further, some embodiments of the present invention prevent bacterial colonization within a fluid pathway of catheter assembly 10 by providing a septum 40 and/or septum actuator 50 having an anti-pathogenic coating material coated thereon. In some instances, an anti-pathogenic material is applied to various surfaces of septum 40 and/or septum actuator 50 which comprise noncritical dimensions. In other instances, an anti-pathogenic material is applied to various surfaces of septum 40 and/or septum actuator 50 which comprise critical and noncritical dimensions. Further still, in some instances an anti-pathogenic material is applied to all surfaces of septum 40 and/or septum actuator 50 which may come in contact with a fluid flowing through a fluid pathway of catheter assembly 10.

As discussed previously, various surfaces of catheter assembly 10 comprise critical dimensions which may be adversely affected by the addition of an anti-pathogenic coating or material. For example, portions of base 52 of septum actuator 50 can comprise critical dimensions configured to fixedly couple septum actuator 50 to catheter adapter 20. Accordingly, in some embodiments it is undesirable to apply an anti-pathogenic material to those portions of base 52. Similarly, in some embodiments it is undesirable to apply an anti-pathogenic material to the outer surface of septum 40, wherein the diameter of the outer surface of septum 40 comprises a critical dimension configured to form an interface with groove 16. Moreover, it may be undesirable to apply an anti-pathogenic material to other such structures, interfaces, and features of the catheter assembly, which comprise critical dimensions.

Catheter adapter 20 further comprises various surfaces which may be coated with an anti-pathogenic material, wherein the surfaces include noncritical dimensions. For example, in some embodiments the inner surface of the distal fluid chamber 32 comprises a noncritical dimension and is therefore coated with an anti-pathogenic material. Similarly, various inner and outer surfaces of probe 54 of septum actuator 50 comprise noncritical dimensions and are therefore coated with anti-pathogenic material. Certain surfaces of proximal fluid chamber 30 further include noncritical dimensions and may therefore be coated with antipathogenic material, as shown. In particular, surfaces disposed proximal to septum 40 comprise noncritical dimensions.

In general, anti-pathogenic material may be applied to any internal or external surface of a medical device, or a component of a medical device, wherein the surface comprises or is exposed to a fluid pathway through the medical device. The surface may further include a critical or non-critical dimension. Pathogens within a fluid passing through the medical device are thus prevented from colonizing within the medical device. In some embodiments, the thickness of the anti-pathogenic material is proportionate to a duration of effectiveness of the anti-pathogenic material on the coated surface. Thus, the duration of effectiveness of the coating may be increased by increasing the thickness of the anti-pathogenic material applied to the surface. The duration of effectiveness may further be modified through modifying the physical properties of the anti-pathogenic material to increase or decrease the rate at which the anti-pathogenic agents are capable of eluting out of the coating material.

As shown, in some embodiments, a rigid or semirigid anti-pathogenic material 60 is selected which is configured to permit long-term elution of the anti-pathogenic agents contained within the material 60. As such, it is desirable to provide the anti-pathogenic material to much of the fluid path surface area of catheter assembly 10. In other embodiments, a viscous, fluid anti-pathogenic material 62 is selected which further comprises a lubricant agent. For example, in some embodiments an anti-pathogenic material 62 is provided which further includes a silicon lubricant agent, such as MED-460 (manufactured by NuSil Technology, LLC). The inclusion of a lubricious agent reduces friction between interfacing components of catheter assembly 10. For example, as further shown, anti-pathogenic material 62 is applied to the probe portion 54 of septum actuator 50, thereby reducing friction between septum actuator 50 and septum 40. In another example, anti-pathogenic material 62 is applied to the outer diameter of septum 40 thereby reducing friction between septum 40 and catheter adapter 20 and permitting septum 40 to slide within internal lumen 26. In some embodiments, anti-pathogenic material 62 further provides a fluid-tight seal between septum 40 and the outer surface of probe 54. Further, in some embodiments, anti-pathogenic material 62 provides a fluid-tight seal to slit 46 of septum 40 prior to activation or provides a fluid-tight seal to slit 46 following removal of probe 54 from septum 40. Still further, in some embodiments, anti-pathogenic material 62 provides between septum 40 and catheter adapter 20.

Anti-pathogenic material 62 may be applied to portions of probe 54 and/or septum 40 prior to assembling catheter assembly 10. In some embodiments, anti-pathogenic material 62 is capable of flowing or migrating when brought into contact with other surfaces. Accordingly, in some embodiments excess anti-pathogenic material 62 from probe 54 is applied to septum 40 following assembly of catheter assembly 10, as shown. In other embodiments, anti-pathogenic material 62 comprises a modified rheology to prevent or control excessive migration of anti-pathogenic material 62 within catheter adapter 20. For example, anti-pathogenic material 62 may further include rheological modifiers to increase the viscosity of the material, such as silica, talc or clay.

The process for coating or applying the anti-pathogenic material to compatible surfaces of catheter assembly 10 may be accomplished by dipping the desired portions or components of the device in their respective coating material 60 and/or 62. Alternatively, anti-pathogenic materials may be sprayed onto the desired surfaces. In some embodiments, surfaces having critical dimensions are masked or otherwise protected prior to applying the anti-pathogenic material to the remaining surfaces. Compatible surfaces may further include a mechanical feature to encourage mechanical binding between the coating material and the compatible surface.

For example, a compatible surface may be designed to include a physical feature that increases mechanical binding of the coating material, such as a texture, a groove, a ridge or some other feature which increases the surface area of the compatible surface. In some embodiments, a mechanical bond is facilitated by a mechanical interlock comprising a void which holds the anti-pathogenic material by capillary force or surface tension forces. In other embodiments, a mechanical interlock comprises a hydrophilic or hydrophobic material or coating that is applied to the compatible surface to attract the anti-pathogenic material.

Further, in some embodiments the anti-pathogenic material is chemically bound to the compatible surface of the catheter assembly or medical device by a chemical bond, such as surface cross-linking. For example, in some embodiments a compatible surface of a device comprises a polymer material that is capable of forming chemical bonds with at least one component of an anti-pathogenic material. Non-limiting examples of polymer materials which may be used to achieve surface cross-linking include polycarbonate, polyester, and polyurethane. In some instances, an anti-pathogenic material is applied to a compatible surface of a device and then cured to achieve surface cross-linking between the anti-pathogenic material and the surface of the device.

Referring still to FIG. 1, for some infusion therapy techniques, air flow between the distal and proximal chambers 32 and 30 may be desirable. For example, for those embodiments comprising a septum 40 having a fluid-tight slit 46, passage of air from the distal chamber 32 to the proximal chamber 30 can be restricted prior to opening or activating the septum 40 with the septum activator 50, as previously discussed. Thus, when the catheter 12 of the catheter assembly 10 is inserted into the vascular system of a patient, a positive pressure develops within the distal chamber 32 thereby preventing a desired flashback of the patient's blood into the catheter adapter 20. An observable flashback is generally desirable to confirm accurate placement of the catheter tip within the vein of the patient. Thus, some embodiments include features or elements to enable airflow between the distal chamber 32 and the proximal chamber 30, without requiring activation of the septum 40 with the septum activator 50. As such, some embodiments of the present invention provide an observable flashback, as generally desired for infusion procedures.

For example, in some embodiments a plurality of air ventilation channel 16 is interposed between septum 40 and the inner surface of catheter adapter 20. Such air vent channels 16 can extend from beyond the distal end of septum 40 to beyond the proximal end of septum 40 when septum 40 is in a pre-actuated position, as shown. The air vent channels 16 can relieve the positive pressure within the distal chamber 32 by providing an access for air to bypass septum 40 into proximal chamber 30. In some embodiments, the air vent channels 16 are constructed by removing portions of the inner surface of the catheter adapter, resulting in a plurality of generally parallel grooves. In some embodiments, air vent channels 16 are sized and shaped to permit airflow, but to restrict fluid flow through air vent channels 16. In other embodiments, air vent channels 16 are sized and shaped to permit airflow and fluid flow, but to restrict fluid flow to less than or equal to a predetermined flow rate. FIG. 2 shows the catheter assembly 10 of FIG. 1, having septum 40 and anti-pathogenic material removed to permit a more clear view of air vent channels 16.

In some embodiments, an anti-pathogenic material is applied to one or more surfaces of the ventilation channel 16, the anti-pathogenic material applied to the surface of the ventilation channel 16 having a thickness less than that which would occlude the ventilation channel 16.

Referring now to FIG. 3, catheter assembly 10 is shown following activation with a Luer adapter 70. Catheter assembly 10 is activated as septum 40 is advanced distally thereby causing probe 54 to pierce through slit 46 of septum 40. In some embodiments, septum 40 is advanced distally as Luer adapter 70 is inserted into opening 56 of catheter adapter 20. In some embodiment, opening 27 (shown in FIG. 2) comprises a diameter and inner wall surface angle that is configured to receive probe 72 of Luer adapter 70 in a friction or interference fit. Accordingly, in some embodiments, it is undesirable to apply an anti-pathogenic material to opening 27, wherein an anti-pathogenic coating would adversely affect the fit of probe 72 within opening 27.

Alternatively, in some embodiments, opening 27 may be coated with an anti-pathogenic material 60 that is viscous, yet fluid enough to be displaced by probe 72 upon coupling of Luer adapter 70 to proximal end 24. In these embodiments, the anti-pathogenic material may act as sealant between probe 72 and opening 27, wherein probe 72 removes the necessary excess amount of anti-pathogenic material to leave a small amount of anti-pathogenic material between the interfacing surface of opening 27 and probe 72.

In some embodiments, an anti-pathogenic material 62 is configured to transfer to interfacing surface within the catheter assembly 10 following activation. For example, in some embodiments, anti-pathogenic material on probe 54 of septum actuator 50 is transferred to septum 50 and the septum slit 46 as probe 54 pierces through slit 46. Further, anti-pathogenic material 60 on septum 40 is transferred to the inner surfaces of internal lumen 26 as septum 40 is advanced distally within catheter adapter 20. Thus, anti-pathogenic material 60 may be applied to various surfaces of catheter assembly 10 in anticipation of further distribution of the anti-pathogenic material following activation of the catheter assembly 10. In other embodiments, anti-pathogenic material 60 comprises a rigid or semirigid material that is not transferred during activation of catheter assembly 10.

In some embodiments, various other structural features and/or surfaces of catheter assembly 10 may include critical dimensions on which it is undesirable to apply an anti-pathogenic material. For example, in some infusion therapy techniques it is desirable to permit a controlled flow of fluid through the septum 40 prior to activating the septum 40. Thus, in some embodiments, slit 46 may further comprise a leak orifice having an opening diameter calculated to permit controlled flow of liquid or air between the proximal and distal fluid chambers 30 and 32. As this leak orifice may include critical dimensions, it may be undesirable to block or reduce the calculated opening diameter by the addition of an anti-pathogenic material.

Figure 4:
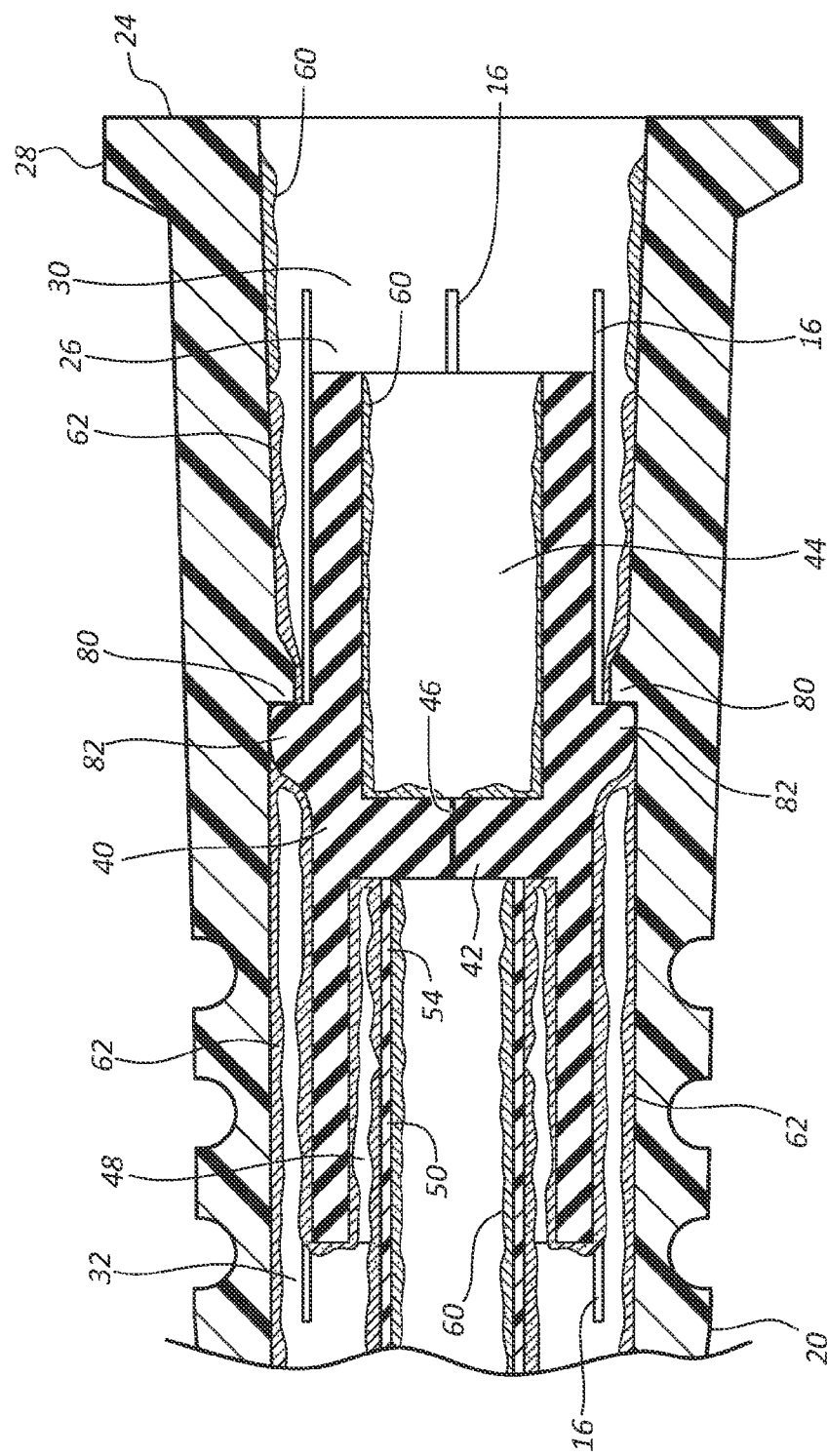
FIG. 4 is a partial, cross-section view of a catheter assembly comprising an alternative septum and septum actuator in accordance with a representative embodiment of the present invention.

Referring now to FIG. 4, a septum 40 is shown within a catheter adapter 20 having structural features to maintain the position of septum 40 within lumen 26 of catheter adapter 20 and thus prevent it from moving out opening 27 in proximal end 24 of catheter adapter 20. For example, in some embodiments, septum 40 comprises one or more fins 82 which can abut a proximal stop 80 of catheter adapter 20 to prevent further proximal movement of septum 40. Fins 82 can comprise any protrusion, hook, latch, or other suitable structure configured to form a barrier surface, such as the illustrated flat proximal surface of fins 82. Proximal stop 80 can include a protrusion extending from the inner surface of catheter adapter 20. Proximal stop 80 can extend radially partially or completely about a portion of internal lumen 26. In some embodiments, to accommodate the one or more fins 56, septum 40 and internal lumen 26 are shaped and sized to provide a gap between septum 40 and internal lumen 26 in which fins 56 and proximal stop 80 reside. As discussed previously, various surfaces of catheter adapter 20 can be coated with an anti-pathogenic material 60 and/or 62. This can include coating portions of the fins 82, proximal stop 80, and portions of the catheter adapter 20 in proximity to the proximal stop 80 and fins 82.

As further shown in FIG. 4, in some embodiments, the septum actuator 50 does not include barbs (e.g., barbs 58 of FIGS. 1-3). Rather, septum 40 can be retained in an activated position (shown in FIG. 3) via forces between septum 40 and septum actuator 50. In other embodiments, septum 40 can return to a pre-activated location (shown in FIG. 1) after removal of the inserted device (e.g., Luer adapter 70 of FIG. 3).

Figure 5:
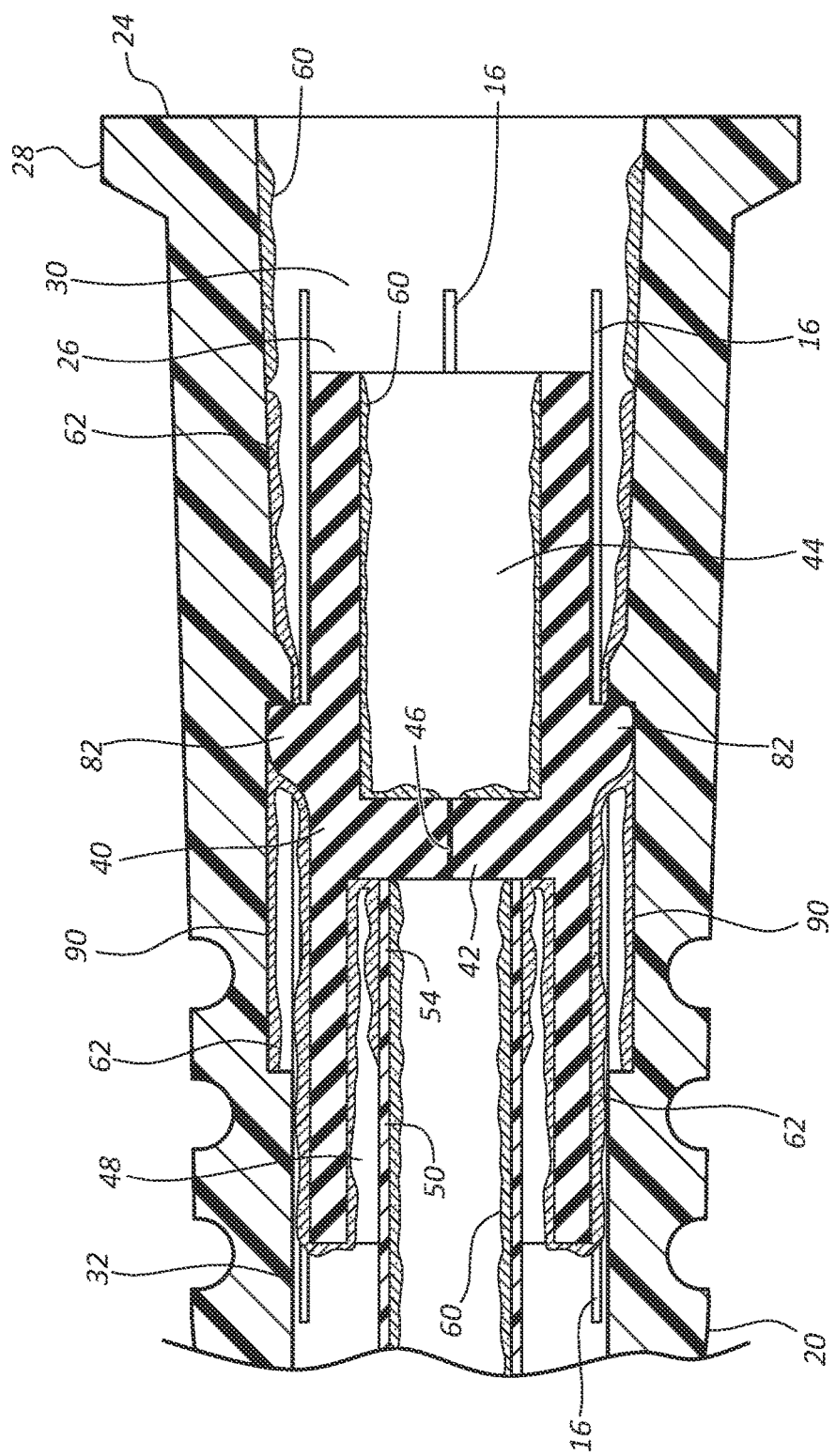
FIG. 5 is a partial, cross-section view of a catheter assembly comprising another alternative septum and septum actuator in accordance with a representative embodiment of the present invention.

Referring now to FIG. 5, an alternative configuration is shown for maintaining the position of septum 40 within lumen 26 of catheter adapter 20 and preventing it from moving out opening 27 in proximal end 24 of catheter adapter 20. As shown, septum 40 includes fins 40, similar to those of septum 40 of FIG. 4. However, the proximal stop 80 of FIG. 4 is replaced with channels 90 or grooves, which are configured to retain a fin 40 therein, while permitting septum 40 to slide proximally during septum activation. Thus, channels 90 can be long enough to accommodate movement of septum 40 from a pre-activation location (e.g., shown in FIG. 1) to an activation location (e.g., shown in FIG. 3). In some embodiments, various surfaces of fins 20 and/or channels 90 can be coated with an anti-pathogenic material 60 and/or 62.

Figure 6:
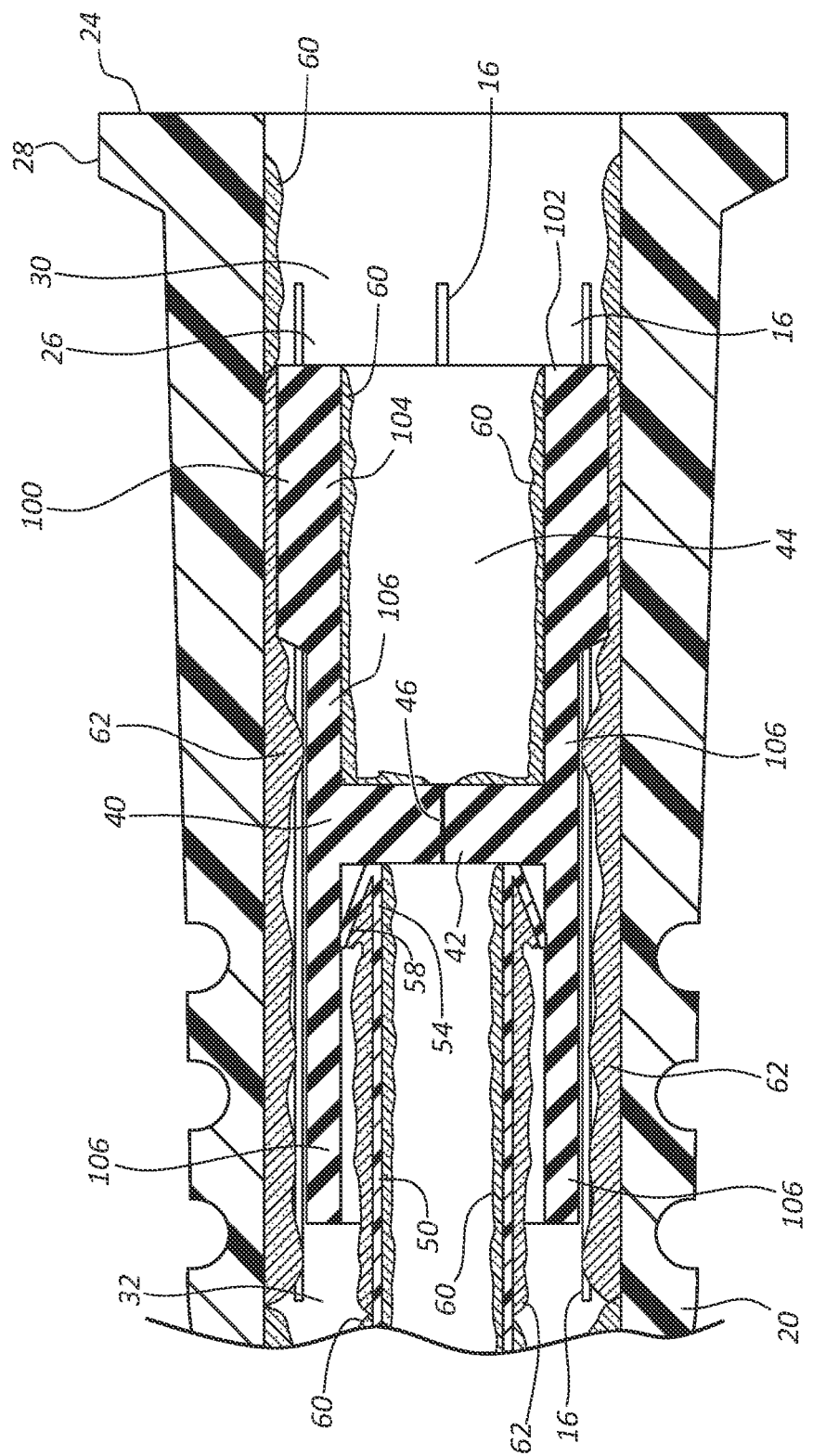
FIG. 6 is a partial, cross-section view of a catheter assembly comprising yet another alternative septum and septum actuator in accordance with a representative embodiment of the present invention.
Figure 7:
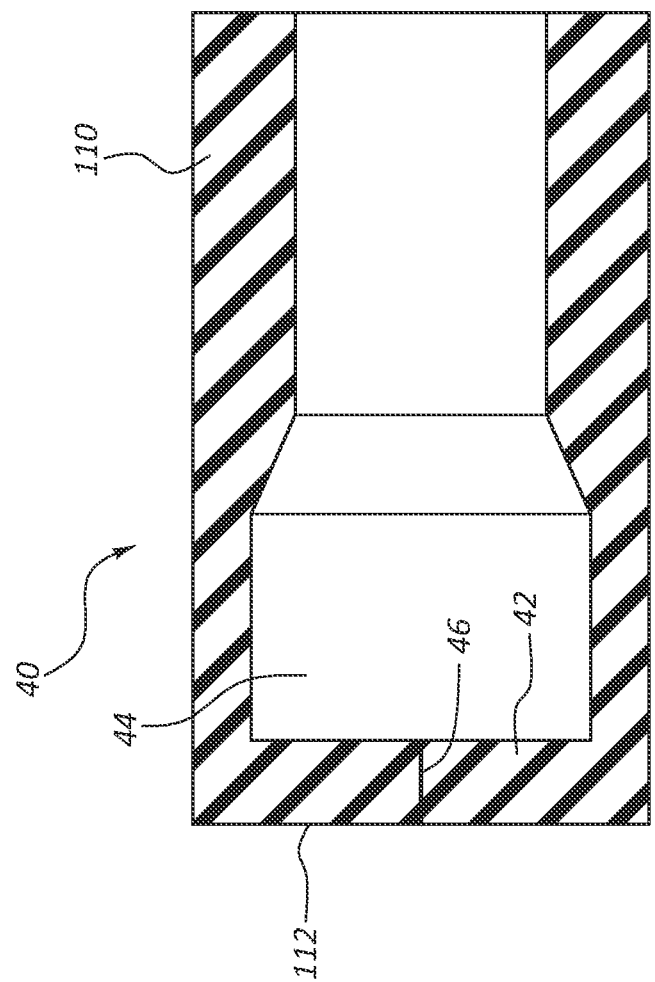
FIG. 7 is a cross-section view of an isolated septum in accordance with a representative embodiment of the present invention.

Referring now to FIG. 6, an alternative septum configuration is shown for providing increased structural support to septum 40 during septum activation. As shown, septum 40 can included a reinforced portion 100 on its proximal end 102. Reinforced portion 100 can assist to prevent septum collapse during septum activation. In general, reinforced portion 100 can include a sidewall 104 having an increased thickness over the remaining sidewalls 106 of septum 40. Reinforced portion 100 can include a thickness of between about 25% to 150% thicker than the remaining sidewalls 106 of septum 40. As shown in FIG. 6, reinforced portion 100 can bulge outwardly from septum 40. FIG. 7 shows an embodiment of a septum 40 having a reinforced portion 110 that bulges inwardly.

FIG. 7 further shows an example of a septum 40 having a barrier member 42 disposed on a proximal end 112 of septum 40. In this configuration, septum 40 does not include a distal cavity (e.g., distal cavity 48 of FIGS. 1 and 3-6). Rather, in such embodiments, septum 40 is retained against probe 54 of septum activator 40 instead of residing within the septum's distal cavity.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A medical device, comprising:
   a fluid pathway;
   a septum slidably housed within the fluid pathway, the septum dividing the fluid pathway into a proximal fluid chamber and a distal fluid chamber; the septum configured to be advanced in a distal direction, to an activated position;
   a septum actuator disposed in a fixed position within the distal fluid chamber of the fluid pathway, the septum actuator extending proximally into the distal fluid chamber, the septum actuator having an outer wall and an inner wall, the inner wall forming a lumen in fluid communication with the fluid pathway;
   a ventilation channel comprising a groove in an inner surface of the medical device, and adjacent the septum; and
   an anti-pathogenic material applied to one or both of the inner and outer walls of the septum actuator, a portion of the anti-pathogenic material further applied to a surface of the ventilation channel, the portion of the anti-pathogenic material applied to the surface of the ventilation channel having a thickness less than that which would occlude the ventilation channel.

2. The device of claim 1, wherein a material of at least one of the device and the septum actuator comprises the anti-pathogenic material.

3. The device of claim 1, wherein the anti-pathogenic material comprises a lubricant.

4. The device of claim 1, wherein the anti-pathogenic material is rigid or semi-rigid.

5. The device of claim 1, wherein the anti-pathogenic material comprises an identifying color to indicate a specific type of the anti-pathogenic material.

6. The device of claim 1, wherein the medical device is a catheter assembly, the catheter assembly forming the fluid pathway between a proximal opening, and a distal end of the catheter assembly, the distal end housing a catheter; wherein the septum is configured to move in a distal direction to an activated position when a separate device is inserted into the proximal opening of the catheter assembly; wherein the septum actuator has a probe and a base, the probe being positioned adjacent to the septum, the base being coupled to the catheter assembly.

7. The device of claim 6, wherein the anti-pathogenic material is applied along the outer wall of the probe but not along the outer wall of the base, and wherein the base comprises critical dimensions configured to fixedly couple the septum actuator to the catheter assembly.

8. The device of claim 1, wherein the septum comprises an inner surface forming a portion of the fluid pathway when the septum is housed within the fluid pathway, the anti-pathogenic material being applied to the inner surface of the septum.

9. The device of claim 1, wherein the anti-pathogenic material comprises a first anti-pathogenic lubricant and a second rigid or semi-rigid anti-pathogenic material.

10. The device of claim 1, wherein the device comprises an inner wall that forms the fluid pathway, the anti-pathogenic material being applied to the inner wall of the device.

11. The device of claim 1, wherein the anti-pathogenic material is applied to at least a portion of the inner and outer walls by at least one of a mechanical bond, and a chemical bond.

12. The device of claim 6, wherein the septum has a tubular shape and a barrier member, the barrier member having a slit extending therethrough.

13. The device of claim 12, wherein the anti-pathogenic material is applied to the barrier member, but not to the slit.

14. The device of claim 6, wherein the septum actuator has barbs on a proximal end of the septum actuator.

15. The device of claim 1, wherein the medical device is an infusion therapy device that includes:
    a ventilation channel disposed between the septum and an inner surface of the infusion therapy device; and
    an anti-pathogenic material applied to a surface of the ventilation channel, the anti-pathogenic material applied to the surface of the ventilation channel having a thickness less than that which would occlude the ventilation channel.

16. A medical device comprising:
    a body having a distal opening, a proximal opening, and a lumen, forming a fluid pathway, extending between the distal and proximal openings, an inner wall of the lumen forming a narrowed portion at the distal opening;
    a slidable septum positioned in the lumen to divide the lumen into a distal chamber and a proximal chamber, the septum comprising an inner surface forming a portion of the fluid pathway when the septum is housed within the fluid pathway; the septum is configured to be advanced in a distal direction to an activated position,
    a septum actuator fixedly positioned in the lumen within the distal chamber, the septum actuator having a base at a distal end that inserts within the narrowed portion of the inner wall and extends proximally into the distal chamber, the septum actuator having an outer wall and an inner wall, the inner wall forming a lumen through which fluid can flow between the distal chamber and the distal opening;
    a ventilation channel comprising a groove in the inner wall of the body, and adjacent the septum; and
    an anti-pathogenic material applied to the inner surface of the septum and to one or both of the inner and outer walls of the septum actuator, a portion of the anti-pathogenic material further applied to a surface of the ventilation channel, the portion of the anti-pathogenic material applied to the surface of the ventilation channel having a thickness less than that which would occlude the ventilation channel.

17. A medical device comprising:
    a body having a distal opening, a proximal opening, and a lumen extending between the distal and proximal openings;
    a septum positioned in the lumen to divide the lumen into a distal chamber and a proximal chamber, the septum being configured to slide in a distal direction within the lumen; a septum actuator that is fixed within the distal chamber such that, when another device is inserted into the proximal opening of the body, the other device forces the septum distally into the septum actuator thereby causing a portion of the septum actuator to pierce the septum forming a fluid path for flow of a fluid through the septum actuator and the body; a ventilation channel comprising a groove in an inner surface of the body, and adjacent the septum; and an anti-pathogenic material applied to an inner surface and an outer surface of the septum actuator, a portion of the anti-pathogenic material further applied to a surface of the ventilation channel, the portion of the anti-pathogenic material applied to the surface of the ventilation channel having a thickness less than that which would occlude the ventilation channel.

18. The medical device of claim 17, wherein the septum actuator comprises a distal base that is coupled to the body and a proximal probe, the anti-pathogenic material being applied to an inner surface and an outer surface of the proximal probe.

19. The medical device of claim 17, wherein the septum has an H-shaped cross-section, the anti-pathogenic material being applied to one or more inner surfaces of the septum.

* * * * *